United States Patent [19]
Hiroshi

[11] Patent Number: 5,639,375
[45] Date of Patent: Jun. 17, 1997

[54] CONCENTRATION OF PESTICIDES BY MEMBRANE PERSTRACTION

[75] Inventor: Nomura Hiroshi, Shorewood, Minn.

[73] Assignee: NeoMecs Incorporated, St. Louis Park, Minn.

[21] Appl. No.: 396,511

[22] Filed: Mar. 1, 1995

[51] Int. Cl.$^6$ ............................................. B01D 61/36
[52] U.S. Cl. ................ 210/640; 210/500.27; 210/500.36
[58] Field of Search .................... 210/643, 638, 210/644, 906, 637, 679, 500.36, 500.27, 640

[56] References Cited

U.S. PATENT DOCUMENTS

| | | | |
|---|---|---|---|
| 3,933,647 | 1/1976 | Muller | 210/346 |
| 4,851,124 | 7/1989 | Vandegrift et al. | 210/638 |
| 4,925,562 | 5/1990 | te Hennepe et al. | 210/500.25 |
| 4,960,520 | 10/1990 | Semmens | 210/640 |
| 5,253,597 | 10/1993 | Swanstrom et al. | 110/346 |
| 5,288,818 | 2/1994 | Livingston et al. | 210/640 |
| 5,290,452 | 3/1994 | Schucker | 210/640 |
| 5,298,669 | 3/1994 | Healy et al. | 568/492 |
| 5,492,838 | 2/1996 | Pawliszyn | 436/178 |

FOREIGN PATENT DOCUMENTS

| | | |
|---|---|---|
| 0559902 | 3/1993 | European Pat. Off. . |
| 06-055166 | 3/1994 | Japan . |
| 2271992 | 5/1994 | United Kingdom . |

OTHER PUBLICATIONS

A. K. Zander et al, "Membrane/Oil Stripping of VOCs from Water in Hollow–Fiber Contactor," J. Environmental Engineering, 115, 768–784 (1989).

A. K. Zander et al, "Removal of Hexachlorocyclohexane Isomers from Water by Membrane Extraction into Oil," Water Research, 26, 129–137 (1992).

*Primary Examiner*—Frank Spear
*Attorney, Agent, or Firm*—Robert J. Petersen

[57] ABSTRACT

Disclosed is a method for concentrating by 20 to 10,000 fold a semivolatile or essentially nonvolatile organic compound, such as a herbicide or pesticide, from a contaminated aqueous solution into a carrier fluid for simultaneous or subsequent analysis. A perstraction membrane is contacted on one surface with a large volume of an aqueous feedstream containing a low concentration of an organic compound, and an opposite surface of the same membrane is contacted with a small volume of a carrier fluid. The perstraction membrane is characterized by a nonporous layer therein which precludes convective flow and mixing between the aqueous and carrier fluid phases. The organic compound is absorbed into the nonporous skin layer from the aqueous fluid and is transferred from the nonporous skin layer into the carrier fluid by an affinity driving force, the affinity of the carrier fluid for the organic compound being greater than the affinity of water for the same compound. The carrier fluid containing the organic compound in concentrated form is passed through a flow cell of an analytical instrument for detection and analysis, or is presented to a sampling port of an analytical instrument, or is otherwise sampled for analysis in a subsequent operation.

18 Claims, 2 Drawing Sheets

CONCENTRATION OF PESTICIDES BY MEMBRANE PERSTRACTION

This invention was made with Government support under contracts No. F41624-92-C-9002 and F41624-93-C-9014 awarded by the Department of the Air Force, Department of Defense. The Government has certain rights in the invention.

FIELD OF THE INVENTION

The present invention relates to a method for concentrating semivolatile and virtually nonvolatile organic compounds from aqueous media by perstraction. More particularly, the present invention relates to the concentration and detection of herbicides and pesticides in groundwaters by perstraction into a nonaqueous fluid.

BACKGROUND OF THE INVENTION

Ground waters are becoming increasingly contaminated by halogenated chemicals, herbicides, pesticides, and various other toxic organic compounds. Sources of contamination include pollution from industrial effluents and accidental chemical spills, leakage of leachates from landfills, and agricultural application of chemicals to crops and soils. Many of these organic compounds are volatile (VOCs) and are capable of removal by air-stripping or vacuum-stripping from groundwaters. More troublesome, on the other hand, are semivolatile organic compounds (SVOCs) and some virtually nonvolatile organic compounds such as polychlorinated biphenyls (PCBs), halogenated pesticides, phosphonate esters such as some herbicides, and the like. These organic compounds are generally sparingly soluble in ground waters. Their concentration levels are often in the part-per-billion range or less. Yet, even such extremely low concentrations represent a potential health hazard because of their bioaccumulative nature. Such low concentrations may be amenable to detection and analysis under carefully controlled laboratory conditions with state-of-the-art instrumentation. Not so readily accomplished, however, is onsite field sampling with simultaneous detection and analysis of such low concentrations.

For example, the U.S. Environmental Protection Agency recommends gas chromatographic analyses for detection of pesticides by established methods (EPA-608{4}, 8151{5}, and 8141A{6}). The method detection limits (MDL) for these analytical techniques are in the range of 0.01 to 1.0 ppb. These methods require large sample volumes and elaborate procedures for collection, preservation, handling and cleaning. To maintain consistency, the expensive gas chromatographs must be calibrated in accord with formal quality control programs. Such methods are inefficient for on-line monitoring of groundwater pollutants. Nor are they appropriate for detection and semi-quantitative monitoring of groundwater contamination. A need remains for efficient preconcentration and sampling techniques combined with sensitive instruments more suited to field sampling sites.

U.S. Pat. No. 4,960,520 discloses a method of removing evaporable contaminants from aqueous solutions by transfer through a gas phase membrane into a stripping solvent. This method involves the use of a microporous membrane having a gas retained in its micropores (hence, the term "gas phase membrane"), with the contaminated aqueous fluid passing in contact with a first face of the membrane and a nonaqueous strippant passing in contact with a second face. A coating of a polymerized disiloxane is deposited on the second face to prohibit penetration of the strippant into the micropores, so as not to displace the entrained gas. This method, being limited to evapotable contaminants, is useful for concentrating volatile organic compounds into a strippant fluid. It has little or no utility for stripping semivolatile compounds because of their low vapor pressure, and appears not to be applicable to virtually (i.e., practically or essentially) nonvolatile compounds such as pesticides and polycyclic aromatic hydrocarbons (PAHs) having Henry's constants of less than about 0.0005 at STP (standard temperature and pressure).

It is an object of this invention to provide a method for concentration of semivolatile and essentially nonvolatile organic compounds from aqueous solutions into an organic solvent.

It is another object of this invention to provide a method by which up to a 10,000-fold concentration of semivolatile or essentially nonvolatile organic compounds may be achieved in an organic solvent in ratio to their aqueous concentrations, starting with highly dilute solutions of the compounds in aqueous solutions such as a contaminated groundwater.

It is an additional object of this invention to provide a method by which onsite field sampling with simultaneous detection and analysis of such low concentrations of semivolatile and essentially nonvolatile organic compounds may be accomplished.

Additional objects, advantages and novel features of the invention will be set forth in the description of the invention which follows, and in part will become apparent to those skilled in the art upon review of the following or as may be learned through practice of the invention.

SUMMARY OF THE INVENTION

It is now found that a membrane perstraction method, to be described herein, can be made to selectively concentrate semivolatile and essentially nonvolatile organic compounds from aqueous fluids. In particular, this method is capable of concentrating halogenated hydrocarbons (such as used in pesticides and herbicides) from contaminated waters by factors as high as 10,000-fold, thereby allowing detection and semiquantitative analysis procedures to be successfully employed at onsite conditions that would have been otherwise less than adequate.

The method of this invention utilizes a membrane concentrator containing a permselective membrane. This membrane is contacted on one surface with a flowing aqueous feedstream containing at least one semivolatile or essentially nonvolatile organic compound. An opposite surface of the same membrane is contacted with a carrier fluid having a higher affinity for the organic compound than water does for the same compound. The permselective membrane is characterized by having on at least one surface thereof a nonporous skin layer which is permeable to the organic compound of interest, but which precludes any convective flow and mixing between the aqueous and carrier fluid phases in contact with the opposite surfaces of the membrane. This nonporous skin layer is preferably in contact with the contaminated aqueous solution which comprises the aqueous feedstream to the concentrator. The carrier fluid is preferably brought into contact with the surface opposite to this nonporous skin layer. Thus, in those types of permselective membranes (e.g., asymmetric and coated composite types) where a porous or microporous matrix is present, any entrained gas in the porous or microporous matrix may be displaced by the carrier fluid, thereby maintaining intimate contact between the carrier fluid and the nonporous skin layer. The organic compound of interest is absorbed into the nonporous skin layer from the aqueous fluid and is transferred from the nonporous skin layer into the carrier fluid by an affinity driving force, the affinity of the carrier fluid for the organic compound being greater than the affinity of water for the same compound. The aqueous feedstream and the carrier fluid are circulated in a continuing manner through the membrane concentrator, whereby the organic compound of interest is transferred in a continuing manner from its aqueous solution to the carrier fluid, causing a build-up of the compound's concentration in the carrier fluid. The carrier fluid containing the organic compound concentrate is passed through a flow cell of an analytical instrument for detection and analysis, or is presented to a sampling port of an analytical instrument, or is otherwise sampled for analysis in a subsequent operation.

The method of this invention preferably employs a two-compartment membrane device, each compartment having inlet and outlet ports. A contaminated aqueous feedstream is passed through one of the two compartments, and a loop including a pump is provided for circulating a carrier fluid through the other compartment. The carrier fluid loop has one or more sampling sites which may optionally be incorporated in the form of a flow cell of an analytical instrument for detection and analysis, or a sampling port of an analytical instrument, other such sampling devices of other analytical instruments, or a sample withdrawal port for removal of an aliquot or essentially all of the carrier fluid for analysis in a subsequent operation. The membrane device preferably employs a bundled hollow fiber membrane, the carrier fluid compartment including the lumen space of the hollow fiber bundle, and the aqueous feedstream compartment including the shell side space surrounding the periphery of the hollow fibers.

By this invention one is able to concentrate essentially nonvolatile organic compounds such as pesticides including DDT, Endrin, and the like, thereby achieving vastly multiplied concentration levels in selected carrier fluids, which are then amenable to analytical detection and quantitation by a variety of instrumental approaches.

DETAILED DESCRIPTION OF THE PREFERRED EMBODIMENT

Figure 1:
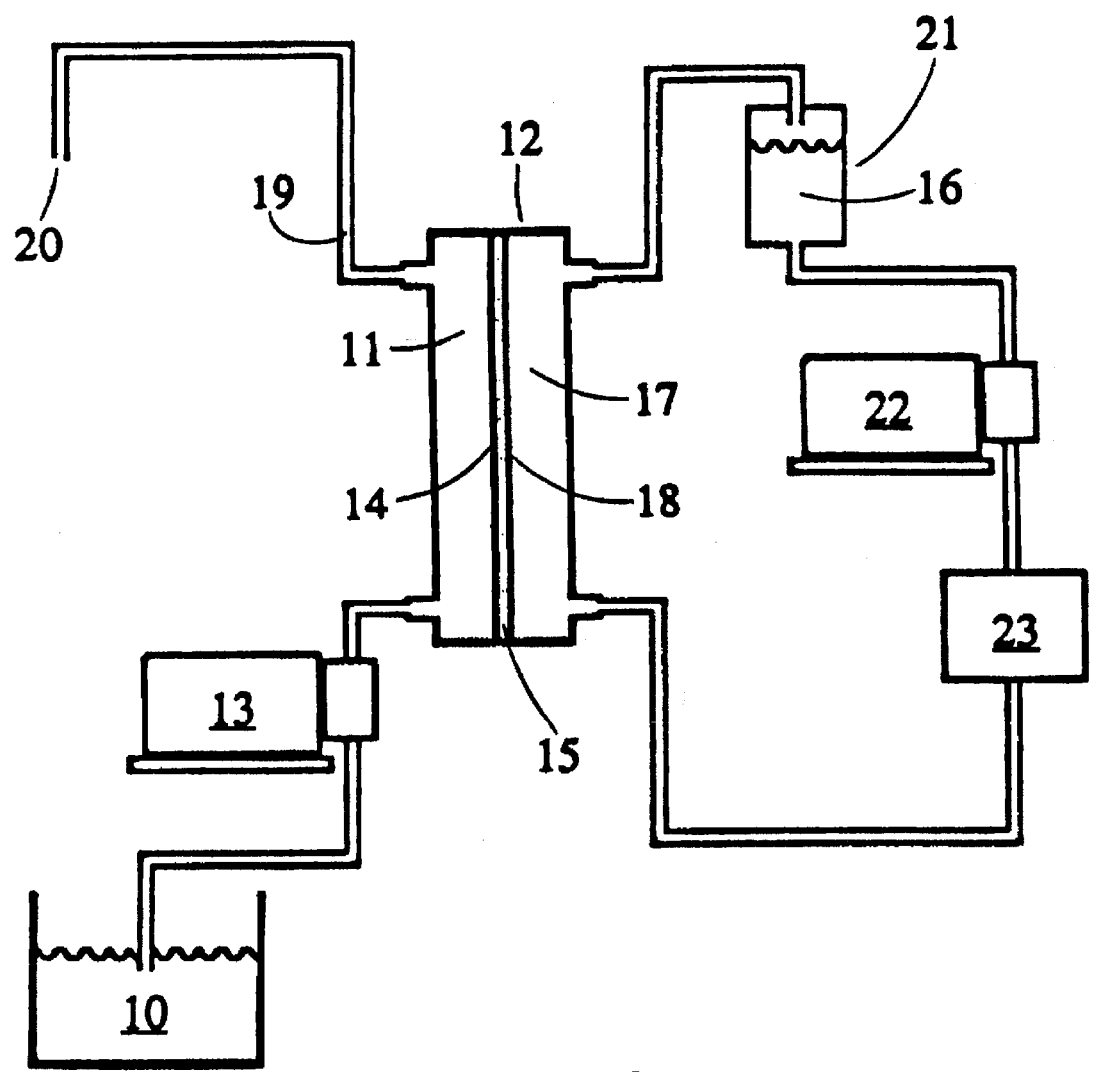
FIG. 1 is a view of a perstraction apparatus for concentrating waterborne semivolatile organic compounds.

Referring to FIG. 1, there is shown an apparatus that can be used in the practice of the invention for concentration of low concentrations of water-borne semivolatile and essentially nonvolatile organic compounds. These compounds are herein defined as organic compounds having a Henry's constant (a dimensionless constant) of less than 0.0005, such compounds including herbicides, pesticides, polychlorinated biphenyls and polycyclic aromatic hydrocarbons. An aqueous feedstream 10 containing at least one such organic compound is fed to a first compartment 11 of a membrane device 12 by a pump 13. In this compartment 11 it comes into contact with a first surface or face 14 of a perstraction membrane 15. This first surface comprises a dense polymeric skin layer. A portion of the organic compound is absorbed from the aqueous feedstream into the skin layer and permeates through this layer, being subsequently taken up by a carrier solvent 16 situated in a second compartment 17 of the membrane device 12, the carrier solvent being in contact with a second surface or face 18 of the perstraction membrane 15. Feedstream 19 that has contacted the membrane 15 is discharged from the membrane device 12, going generally to a discharge outlet 20. The carrier solvent 16 is preferably circulated through the membrane device 12 from a reservoir 21 by means of a solvent pump 22, and this circulation of the carrier solvent is preferably continued simultaneously as the aqueous feedstream is fed to the membrane device. The carrier solvent 16 becomes enriched in the organic compound with continued inflow of the feedstream and circulation of the carrier solvent itself. The concentration of the organic compound rises toward an asymptotic equilibrium value in the carrier solvent with time. At least a portion of the carrier solvent containing the organic compound may be subsequently sampled for analysis or passed into or through an analytical instrument for online detection and/or identification of the organic compound. Alternatively, essentially all of the carrier solvent containing the organic compound may be removed from the apparatus through a sample port 23 and analyzed in a subsequent operation.

Figure 2:
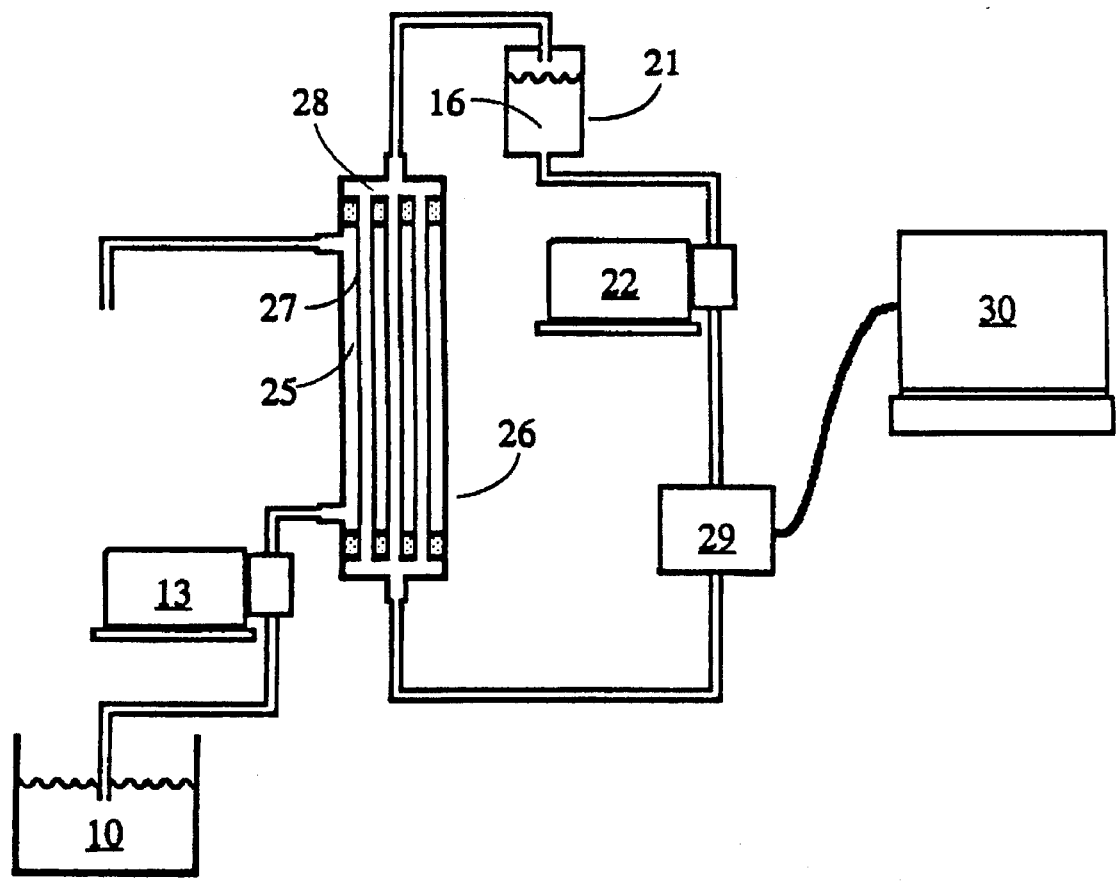
FIG. 2 is a view of an apparatus for simultaneous perstraction and analytical detection of organic compounds.

Referring to FIG. 2, an alternate embodiment is shown in the form of an apparatus that can be used in the practice of the invention for simultaneous concentration and detection and/or analysis of low concentrations of water-borne semivolatile and essentially nonvolatile organic compounds such as herbicides, pesticides, polychlorinated biphenyls and polycyclic aromatic hydrocarbons. An aqueous feedstream 10 containing at least one semivolatile or essentially nonvolatile organic compound is fed by a pump 13 to a first compartment 25 of a membrane device, optionally shown here as a hollow fiber permeator 26, wherein it comes into contact with the outer surface of one or more hollow fiber perstraction membranes 27, following which it is discarded. A portion of the organic compound permeates through the membrane and is taken up by a carrier solvent 16 situated in a second compartment 28 of the hollow fiber permeator or 26, wherein the second compartment consists in part in the lumen space of the hollow fiber or fibers. The carrier solvent 16 is preferably circulated continuously through the hollow fiber membrane device 26 from a reservoir 21 by means of a solvent pump 22 as the feedstream is fed to the membrane device. The carrier solvent 16, enriched in the organic compound by perstraction from the feedstream 10, is circulated through a sampling device 29 of an analytical instrument 30 for online detection and/or identification of the organic compound. The sampling device may consist of a sampling port to an analytical instrument or a flow cell of an analytical instrument, for example. But these examples are not meant to limit the scope of such sampling devices, in that various types of analytical instruments will necessarily involve various types of sampling devices. The analytical instrument may consist, for example, of an ultraviolet light (UV) absorption spectrophotometer, a Fourier transform infrared (FTIR) absorption spectrophotometer, a mass spectrum analyzer, a surface enhanced Raman spectrophotometer (SERS), a gas chromatograph, or any of a number of other analytical devices. Similarly as before, an aliquot or essentially all of the carrier solvent 16 containing the organic compound may be removed from the apparatus through the sampling device or a separate sampling port (not shown) and may be analyzed in a separate, subsequent operation.

The membrane device may consist of any of a variety of designs, including such designs that incorporate membrane in the form of a flat plate, a tube, a flat sheet in a spirally wound assembly, or a hollow fiber. Membrane devices employing membrane in the shape of hollow fibers bundled together are particularly preferred. Hollow fiber designs tend to have the highest surface to volume ratio of active membrane among the various alternative membrane devices, thereby often achieving the greatest efficiency of mass transfer through the overall membrane device. Advantages enhanced thereby include: minimizing the volume of carrier solvent required for operation, minimizing the amount of feedstream to be pumped through the membrane device, and shortening the time necessary to approach the asymptotic equilibrium value of concentration build-up of the perstracted organic compound in the carrier solvent. It is particularly desirable to minimize the amount of carrier solvent necessary to conduct the perstraction, such as a volume of 100 milliliters or less, more preferably about 20 ml or less, most preferably 12 ml or less, of carrier solvent. Thus, a preferred apparatus will be characterized by a low overall priming volume, which is achievable through a membrane device such as a hollow fiber design with lumen flow of the carrier fluid, and through careful selection of pump, tubing, and reservoir components for circulation of the carrier solvent through the membrane device.

The membrane to be employed in the membrane device may consist of an isotropic, an asymmetric, or a composite type. An isotropic membrane is commonly characterized by a homogeneous chemical nature throughout its wall thickness, and a dense wall matrix. An asymmetric membrane is commonly characterized by a homogeneous chemical nature throughout its wall thickness, but with a wall matrix that gradates from a thin dense skin layer to a porous supporting layer. Both sides of such a membrane may, in some instances, be skinned, though such is not a preferred aspect for the practice of this invention. A composite type of membrane is commonly characterized by a nonhomogeneous chemical nature as well as a nonhomogeneous wall matrix, typically having a thin skin of one chemistry deposited upon one surface of a porous substrate of another chemistry. For this composite membrane, porous substrates made of polymeric compositions such as polyolefins, substituted polyolefins, polysulfone or aromatic condensation polymers are generally well suited. Microporous polypropylene hollow fibers have been found to be particularly advantageous as porous substrates. Such fibers are commercially available from at least two sources, these being Hoechst Celanese Corporation, maker of Celgard X20-240 and X20-400 hollow fibers, and Mitsubishi Rayon Company, maker of KPF 190M, 270B, 360A, 250M and 190G hollow fibers. These hollow fibers have pores that are generally elliptical in shape, due to the nature of their generation by drawing and stretching processes. The length of such pores may vary up to about 6000 angstroms, the width being at least 10 angstroms and varying up to 650 angstroms or more. Mitsubishi KPF 190M polypropylene hollow fibers have been found to be particularly preferred as substrates for use in making composite membranes suitable for the concentration method described herein.

The thin skin of polymeric material may be deposited on a suitable porous substrate by methods such as by dipping, spraying, or the like. It has been found preferable in the practice of this invention to deposit the thin skin by means of plasma polymerization of a polymerizable monomer. Thus, a suitable porous substrate is brought into contact with a glow discharge gas plasma containing a polymerizable monomer, and a plasma polymerizate is deposited on an exposed surface of the substrate for a time sufficient to close off surface pores in the substrate. Particularly preferred are plasma polymerizates formed from glow discharge gas plasmas containing one or more siloxane monomers, whereby the plasma polymerizate consists, in large part, of a crosslinked polysiloxane deposit. Examples of such a membrane are disclosed in U.S. Pat. Nos. 4,410,338 and 4,824,444, which are hereby incorporated by reference. Also preferred is a composite membrane consisting essentially of a crosslinked polysiloxane deposited from a gas plasma containing a siloxane monomer onto a porous substrate such as a microporous polypropylene hollow fiber, wherein the surface of the polysiloxane deposit has been further modified by deposition of a permeable coating of a fluorinated plasma polymerizate, whereby concomitant water transport through the membrane is reduced. A necessary attribute of the membrane is that it preclude convective flow of liquids from either of its surfaces to the other surface, so that transport of the semivolatile or essentially nonvolatile organic compound (i.e., compounds characterized by a Henry's constant of less than 0.0005) through the membrane involves firstly a desolvation of this compound from the aqueous phase at the membrane-feedstream interface, diffusion of the compound through the nonporous layer of the membrane, and solvation of the compound in the carrier fluid.

The carrier fluid is preferably a nonaqueous liquid. The carrier fluid preferably has a high affinity for a semivolatile organic compound of interest. Affinity may be judged by the solubility of the organic compound in the carrier fluid and the ratio of this solubility to the organic compound's solubility in the aqueous feedstream being accessed by the membrane device. As an example, if a potential concentration factor of 1000-fold is desired for an organic compound, which is present in an aqueous feedstream at a threshold concentration of 1 ppb (1 mcg/l), then the carrier fluid preferably exhibits a minimum solubility power of 10 parts per million (10 mg/l) toward the organic compound. The carrier solvent also preferably, though not necessarily, has a low solubility in water, a low permeation rate through the membrane skin, and a low vapor pressure. These characteristics would serve to minimize any loss of the carrier fluid during the operation of the method of the invention. The carrier fluid also preferably has a low affinity for water, such that water transport through the membrane from the aqueous feedstream to the carrier fluid is not promoted or enhanced. A few examples of the broad range of applicable nonaqueous carrier fluids that may be used include polyethylene glycol, 1-octanol, silicone oil, and perfluorinated 3-pentyl-tetrahydrofuran. The carrier fluid may be aqueous in nature, however, if it contains one or more ingredients that cause an aqueous carrier fluid to have a much higher affinity for the semivolatile organic compound than the incoming aqueous feedstream in which the organic compound is initially contained.

The carrier fluid ideally will not interfere with the detection and analysis of the semivolatile organic compound by a detector or analytical instrument. A silicone oil, for example, generally presents a clear window to ultraviolet light for UV detection of herbicides and pesticides. If sampling of the carrier solvent is desired for gas chromatographic analysis, however, a vaporizable solvent such as the 1-octanol may be more desirable to a silicone oil, which is generally not as vaporizable.

The flow rate of feedstream through the perstraction membrane device may be varied widely. The optimum flow rate will depend in great part on the type, shape and size of the membrane device. It is wig the capability of one of ordinary skill in the art to determine by minimal experimentation a satisfactory range of feedstream flow rate to employ.

The cumulative volume of feedstream to pass through the perstraction device to achieve good results may also be varied. The cumulative volumetric ratio of feedstream to carrier fluid volume is preferably 1,500 or greater. In field sampling of a contaminated groundwater, volumetric ratios far greater than 1,500 are possible, and may accrue to 10,000 or even 100,000. Lesser volumetric ratios, from 40 to 1,500, may be employed in industrial or laboratory situations where feedstream volumes are sometimes in limited quantity. In such cases the concentrating factor achievable for the perstraction device may not be fully developed. Generally, as in the case of a contaminated groundwater, the aqueous feedstream is passed through the membrane device in a single pass mode of operation. One may, however, recirculate an aqueous feedsteam from a reservoir through the membrane device in a multiple pass (i.e., loop mode) of operation. Flow of the feedstream and of the earlier fluid may be co-current or counter-current. Counter-current flow of the two fluids along opposite sides of the perstraction membrane is generally preferable, but co-current flow of the two fluids is fully acceptable in the practice of this invention.

In a conventional perstraction used for purposes other than now being disclosed herein, the removal of those components that diffuse through the membrane to the downstream side (i.e., permeate side) of the membrane is accomplished by use of a liquid sweep stream. The use of the sweep stream keeps the concentration of the components at the permeate side of the membrane low and maintains the concentration gradient which is partially responsible for the transfer of the components through the membrane. Such usage tends to require significant volumes of sweep stream fluid, both to enhance sweeping flow and to minimize concentration build-up in the sweep fluid. In the practice of this invention, however, a desired attribute is the development of as high a concentration as possible in the carrier fluid to aid detection and analysis. It is preferable in this invention, therefore, to minimize the amount of carrier solvent needed to conduct the perstraction. Furthermore, when an effective affinity driving force is present for movement of the organic compound through the membrane, and the organic compound is at sub-part-per-million concentrations in the aqueous feedstream, little or no advantage is gained in sweeping the carrier fluid through the membrane device at a high flow rate intended to minimize permeate side concentration of the diffused component, in contrast to conventional perstraction practice.

The use of applied hydrostatic pressure on either the aqueous feedstream or the carrier fluid is not critical, since the perstraction precess is not dependent on pressure as a driving force for transfer of the organic compound from the aqueous solution to the carrier fluid. Generally, sufficient pressure to cause the fluids to flow through the apparatus is all that is needed.

The perstraction process may be run at any convenient temperature within the normally liquid range of water, i.e., normally between 0 and 100 degrees Celsius. The perstraction is preferably run at a temperature in the range of 10 to 40 degrees Celsius.

An apparatus used in conducting perstractions according to this invention preferably does not contain components, other than the membrane and the carrier fluid, that absorb the organic compounds of interest and thus deplete or diminish the amount concentratable into the carrier fluid. In particular, the carrier fluid loop comprising a pump, tubing and a reservoir is ideally constructed with stainless steel, glass, and/or polytetrafluoroethylene components. Other materials may be used as well, but may entail testing for their suitability.

The following specific examples are given as illustrative of a preferred embodiment of the invention as contemplated by the inventor, but should not be taken to represent the limits of the practice of the invention.

Preparation of Perstraction Membranes

A composite perstraction membrane herein designated as a Type 1 membrane was prepared by coating a microporous polypropylene hollow fiber on its exterior surface with a polysiloxane polymerizate deposited form a glow discharge gas plasma containing a disiloxane monomer. A microporous polypropylene hollow fiber (KPF 190M, obtained from Mitsubishi Rayon Company) was passed through a gas plasma formed by means of a 13.58 MHz radiofrequency glow discharge through a 50 mtorr gaseous blend of hexamethyldisiloxane and air in a vacuum chamber at a power level of 100 watts. Disiloxane monomer flow rate into the vacuum apparatus was 1.46 sccm and air flow rate was 3 sccm. The hollow fiber was unwound from a supply spool and passed through the gas plasma zone 17 times for a total exposure time of about 75 seconds before being wound upon a product spool. Typical gas permeability data for this Type 1 membrane included oxygen, nitrogen and carbon dioxide permeation rates of $1.32 \times 10^{-4}$, $0.57 \times 10^{-4}$ and $5.48 \times 10^{-4}$ $cm^3/cm^2$-sec-cmHg, respectively, tested on the individual gases at 10 psig, with a corresponding oxygen/nitrogen selectivity ratio of 2.3 and a carbon dioxide/nitrogen selectivity ratio of 9.7. Such data indicated the presence of a nonporous polysiloxane skin layer on the microporous polypropylene substrate. A water transport rate measured through a Type 1 polysiloxane polymerizate-coated membrane was $6.55 \times 10^{-6}$ $cm^3/cm^2$-sec-cmHg.

A Type 2 composite perstraction membrane with reduced water permeability was prepared by passing a polysiloxane polymerizate-coated polypropylene fiber of a type generally as above through a glow discharge gas plasma containing a polymerizable fluorocarbon monomer in a vacuum chamber. Thus, a Type 1 hollow fiber membrane prepared as above was passed through a gas plasma formed by means of a 13.58 MHz radiofrequency glow discharge through a 100 mtorr vapor of tetrafluoroethylene at a power level of 25 watts. The tetrafluoroethylene was fed to the vacuum chamber at a rate of 8.25 sccm. Calculated power input W/FM was $4.1 \times 10^7$ J/kg. The hollow fiber composite membrane was passed through the plasma polymerization zone a total of 17 times to give a total effective residence time in the plasma zone of about 75 seconds. The resulting composite membrane had an overcoating of a polyfluorinated plasma polymerizate on the polysiloxane polymerizate's exterior surface. Typical gas permeability data for this Type 2 membrane included oxygen, nitrogen and carbon dioxide permeation rates of $1.74 \times 10^{-4}$, $0.93 \times 10^{-4}$ and $5.65 \times 10^{-4}$ $cm^3/cm^2$-sec-cmHg, respectively, tested on the individual gases at 10 psig, with a corresponding oxygen/nitrogen selectivity ratio of 1.8 and a carbon dioxide/nitrogen selectivity ratio of 6.1. Water transport rate measured through a Type 2 composite perstraction membrane was $3.85 \times 10^{-6}$ $cm^3/cm^2$-sec-cmHg, measured on the same basis as for the above-described Type 1 membrane.

EXAMPLE 1

A series of perstractions was run at a variety of volumetric flow rates and organic compound concentrations, using 2,4-dichlorophenoxy acetic acid (CAS Reg. No. 94-75-7) as an organic contaminant in water and polyethylene glycol (average molecular weight ca. 200) as the carrier fluid, to demonstrate the concentrative effects of this method. A hollow fiber module was prepared containing 100 fibers of a Type 1 membrane and having an effective membrane length of 14 cm. Nitrogen, oxygen and carbon dioxide permeabilities of the membrane were approximately 1.4, 3.5 and $17 \times 10^{-4}$ $cm^3/cm^2$-sec-cmHg respectively. The aqueous feedstream containing 2,4-dichlorophenoxy acetic acid was pumped through the shell side of the hollow fiber membrane device, being continuously recycled to a reservoir. The polyethylene glycol carrier fluid was circulated from a separate reservoir through the lumen of the hollow fiber module at one ml/min. Volumetric ratio of feedstream to carrier fluid was varied between 28 and 1514. The concentration of 2,4-dichlorophenoxy acetic acid ranged from 25 ppm at the low end of volumetric ratio to 0.5 ppm at the high end of volumetric ratio. Samples of 2 ml each were periodically withdrawn from the carrier fluid for analysis of the content of 2,4-dichlorophenoxy acetic acid. Results of this series of runs are shown in Table 1. It was found that at high concentrations (such as 25 mg/l) of 2,4-dichlorophenoxy acetic acid in the aqueous feedstream, concentration in the carrier fluid reached a maximum in 15 minutes or less. At low concentrations such as 0.5 to 2 mg/l of this organic compound, high volumetric ratios were needed to approach the same maximum value, requiring between 15 minutes and 1 hour to do so at the stated flow rates. Concentration factors were calculated based on initial feedstream concentration. Concentration factors as high as 1864, on that basis, were obtained in the perstraction of 2,4-dichlorophenoxy acetic acid from water into polyethylene glycol 200, when the initial feed concentration in the recirculated aqueous feedstream was 0.5 mg/l.

EXAMPLE 2

In the same manner as in Example 1, a series of perstractions was run wherein the aqueous feedstream was varied to contain either 2,4-dichlorophenoxy acetic acid, Chlorpyrifos [O,O-diethyl O-(3,5,6-trichloro-2-pyridyl)phosphorothiate, CAS Reg. No. 2921-88-2], or Endrin [O,O-diethyl O-(6-methyl-2-{1-methylethyl)-4-pyrimidinyl}) phosphorothiate, CAS Reg. No. 2921-88-2]at concentrations of 0.5, 0.2 and 0.1 mg/l respectively. A hollow fiber module containing 150 fibers of the same type of membrane as in Example 1 was used. The carrier fluid was polyethylene glycol 200. Samples of 1.5 to 2 ml each were periodically withdrawn from the carrier fluid for analysis of the content of each organic compound. Results of this series of runs are shown in Table 2. Concentration factors as high as 2925 were obtained, based on initial feedstream concentration. When concentration factors were corrected for decreases in the feedstream organic contents based on mass balance calculations, the corrected concentration factors were approximately 3000, 19000 and 4000 for 2,4-dichlorophenoxy acetic acid, Chlorpyrifos and Endrin respectively. These values appeared to be reasonably related to solute distribution phenomena between polyethylene glycol 200 and water for these organic compounds.

TABLE 2

| Organic Compound | Feed Conc. (mg/l) | Run Time (min) | Feedstream Volume (ml) | Feedstream Flow (ml/min) | Carrier Solvent Volume (ml) | Carrier Solvent Conc. (mg/l) | Concentration Factor |
|---|---|---|---|---|---|---|---|
| 2,4-dichlorophenoxy acetic acid | 0.5 | 6 | 18,000 | 1,200 | 12 | 390 | 780 |
| | | 12 | | | 10 | 408 | 816 |
| | | 18 | | | 8 | 459 | 918 |
| | | 30 | | | 6 | 658 | 1,316 |
| Chlorpyrifos | 0.2 | 6 | 18,000 | 1,200 | 12 | 386 | 1,950 |
| | | 12 | | | 10.5 | 253 | 1,265 |
| | | 18 | | | 9 | 337 | 1,685 |
| | | 24 | | | 7.5 | 365 | 1,825 |
| | | | | | 6 | 585 | 2,925 |
| Endrin | 0.1 | 6 | 18,000 | 1,200 | 15 | 132 | 1,320 |
| | | 12 | | | 13.5 | 115 | 1,150 |
| | | 18 | | | 12 | 121 | 1,210 |
| | | 24 | | | 10.5 | 127 | 1,270 |
| | | 30 | | | 9 | 125 | 1,250 |

EXAMPLE 3

A hollow fiber module was connected to a feedstream loop on the shell side of the membrane and a carrier fluid loop on the lumen side of the membrane. The hollow fiber membrane in the module consisted of the Type 2 membrane. The feedstream loop consisted of a 2 liter reservoir of water solution, a pump, a flowmeter, the membrane device, a pressure regulator, stainless steel tubing connections between these components, and a return line to the reservoir. The carrier solvent loop consisted of a reservoir, a pump, the membrane device, a 254 nm flow cell connected to a UV spectrophotometer (Beckman Model DU 640), stainless steel capillary tubing connections between these components, and a return line to the reservoir. The carrier fluid was silicone oil (10 cp grade), and about 18.6 ml was placed in the carrier fluid loop. Two liters of 2.5 ppm (2.5 mg/l) aqueous Diazinon solution were placed in the feedstream loop, and were circulated through the membrane device at a flow rate of 600 ml/min. Circulation rate of the silicone oil was 1 ml/min. Diazinon concentration in the silicone oil rose to 135 ppm (135 mg/l) in 270 minutes of perfusion of the module by the aqueous feedstream. Feedstream concentration declined to 0.65 ppm, as measured by UV in a stationary cell. The final concentration ratio of Diazinon in the carrier fluid versus the feedstream was 208.

EXAMPLE 4

In the same manner as described in Example 3, an aqueous solution of 2.0 ppm 2,4-dichlorophenoxy acetic acid was perstracted into a 22.4 ml volume of 1-octanol as the carrier fluid. Perfusion rate of aqueous feedstream to the membrane device was 300 ml/min. The 2,4-D concentration in the 1-octanol rose to 130 ppm over a 30 minute perfusion time.

EXAMPLE 5

A hollow fiber module containing the Type 1 membrane was connected to a feedstream loop on the shell side of the membrane and a carrier solvent loop on the lumen side of the membrane, and a perstraction was run in the same manner as described in Example 3. An aqueous solution of 0.2 ppm polychlorinated biphenyl (PCB-1242, CAS Reg. No. 53469-21-9) was perstracted into a 23.6 ml volume of silicone oil over a period of 170 minutes. PCB concentration in the silicone oil rose to an asymptotic level of about 8.5 ppm, and the carrier fluid/feed concentration ratio peaked at about 80 after a period of 170 minutes.

EXAMPLE 6

A perstraction was conducted with a aqueous feedwater containing a pair of herbicides (Chlorpyrifos and Diazinon) and an online UV detection and analysis instrument. Initial aqueous herbicide concentrations were set at 100 ppb (0.1 mg/l) to achieve sufficient build-up of the organic compounds in the carrier fluid to allow actual concentration measurement by the UV spectrophotometer (Beckman Model DU 640). A hollow fiber module containing approximately 930 $cm^2$ of active membrane surface area of a Type 1 composite membrane was perfused on the shell side of the fibers with a feedstream of water containing 0.1 ml/l of Chlorpyrifos and 0.1 mg/l of Diazinon. The aqueous feedstream was fed at 800 ml/min and 7.3 psig hydrostatic pressure to the membrane device and recirculated to reservoir containing 2 liters of the aqueous solution. The carrier fluid was silicone oil (25 cp grade). It was recirculated through the lumen side of the membrane device at a rate of 1 ml/min, then through a pair of UV detector flow cells, one connected to a 254 nm wavelength detector and the other to a 280 nm wavelength detector. Carrier fluid volume was about 24.2 ml. After 110 minutes of circulation, the concentration of Chlorpyrifos had risen to 7.8 mg/l in the carrier fluid, while falling to about 0.0056 mg/l (calculated) in the feedstream, resulting in a calculated concentration ratio of 1393. The concentration of Diazinon had risen to 6.2 mg/l in the carrier fluid, while falling to about 0.025 mg/l (calculated) in the feedstream, resulting in a calculated concentration ratio of 248. The perstraction was repeated with a fresh solution of Chlorpyrifos and Diazinon, pumped at 800 ml/min through the hollow fiber module, and at 30 psig hydrostatic pressure instead of 7.3 psig. Silicone oil volume was about 22.2 ml, and perstraction time was 90 minutes. Final concentration of the semivolatile herbicides in the silicone oil were 8.4 mg/l for Chlorpyrifos and 4.2 mg/l for Diazinon, corresponding to calculated concentration ratios of 1235 and 79 respectively. In this example, the analytical instrument was able to simultaneously detect and measure concentrations of the two herbicides, present as a mixture in the silicone oil carrier fluid.

TABLE 1

| Feed Conc. (mg/l) | Run Time (min) | Feedstream Volume (ml) | Flow (ml/min) | Carrier Solvent Volume (ml) | Carrier Solvent Conc. (mg/l) | Concentration Factor |
|---|---|---|---|---|---|---|
| 25 | 15 | 1,300 | 484 | 46 | 500 | 20 |
|  | 30 |  |  | 41 | 500 | 20 |
|  | 60 |  |  | 36 | 450 | 18 |
| 2.5 | 15 | 2,000 | 220 | 46 | 210 | 84 |
|  | 30 |  |  | 41 | 210 | 84 |
|  | 60 |  |  | 36 | 210 | 84 |
| 2.0 | 5 | 2,000 | 186 | 50 | 140 | 70 |
|  | 10 |  |  | 48 | 141 | 71 |
|  | 15 |  |  | 46 | 130 | 65 |
| 0.5 | 0 | 11,355 | 900 | 40 | 0 | 0 |
|  | 9 |  |  | 37.8 | 50 | 100 |
|  | 15 |  |  | 35.6 | 137 | 274 |
| 2.0 | 0 | 11,425 | 880 | 40 | 0 | 0 |
|  | 7.5 |  |  | 37.5 | 223 | 112 |
|  | 15 |  |  | 35.4 | 390 | 195 |
| 0.5 | 15 | 75,700 | 680 | 50 | 173 | 346 |
|  | 30 |  |  | 47.4 | 223 | 446 |
|  | 60 |  |  | 45 | 418 | 836 |
|  | 115 |  |  | 42.6 | 390 | 780 |
| 0.5 | 10 | 20,000 | 400 | 12 | 202 | 404 |
|  | 20 |  |  | 10 | 325 | 650 |
|  | 30 |  |  | 8 | 195 | 390 |
|  | 50 |  |  | 6 | 542 | 1084 |
| 0.5 | 6 | 20,000 | 800 | 12 | 325 | 650 |
|  | 12 |  |  | 10 | 245 | 490 |
|  | 18 |  |  | 8 | 282 | 564 |
|  | 25 |  |  | 6 | 570 | 1140 |
| 0.5 | 4 | 20,000 | 1,200 | 12 | 382 | 764 |
|  | 8 |  |  | 10 | 412 | 824 |
|  | 12 |  |  | 8 | 491 | 982 |
|  | 16 |  |  | 6 | 932 | 1864 |
| 0.5 | 3 | 20,000 | 1,600 | 12 | 137 | 274 |
|  | 6 |  |  | 10 | 303 | 606 |
|  | 9 |  |  | 8 | 202 | 404 |
|  | 12 |  |  | 6 | 664 | 1328 |

I claim:

1. A method of concentrating an organic compound from an aqueous solution comprising: a) bringing an aqueous solution containing an organic compound into contact with a first surface of a nonporous skin layer of a perstraction membrane, the nonporous skin layer having a first and a second surface, the perstraction membrane comprising a nonporous skin layer supported on its second surface by a microporous substrate, b) circulating a carrier fluid in contact with the second surface of said nonporous skin layer, the microporous substrate also being filled with the carrier fluid, and c) transferring by perstraction a portion of the organic compound from the aqueous solution through said nonporous skin layer to the carrier fluid, wherein the organic compound has a Henry's constant of less than 0.0005, wherein the organic compound is transferred through said nonporous skin layer by an affinity driving force.

2. The method according to claim 1 wherein the organic compound is concentrated to a concentration level in the carrier fluid that is 20 to 10,000 fold greater than its concentration in the aqueous solution.

3. The method according to claim 2 wherein the concentration of the organic compound in the carrier fluid is measured by passing the carrier fluid through a sampling device of an analytical instrument.

4. The method according to claim 3 wherein the membrane is contained in a membrane device having a first compartment for flow through of the aqueous solution and a second compartment for flow through of the carrier fluid.

5. The method according to claim 4 wherein the membrane is in the form of a hollow fiber.

6. A method of concentrating an organic compound from an aqueous solution comprising:
   a) bringing in a continuing manner an aqueous solution containing an organic compound having a Henry's constant of less than 0.0005 into contact with a first surface of a nonporous skin layer of a perstraction membrane, the nonporous skin layer having a first and a second surface, the perstraction membrane comprising a nonporous skin layer supported on its second surface by a microporous substrate, b) circulating a carrier fluid in contact with the second surface of the nonporous skin layer, and c) transferring in a continuing manner by perstraction a portion of the organic compound from the aqueous solution through the nonporous skin layer to the carrier fluid until the organic compound attains a concentration level in the carrier fluid that is at least 20-fold its concentration level in the aqueous solution, wherein the carrier fluid has an affinity for the organic compound that is greater than the affinity of water for the organic compound, the organic compound being transferred through the nonporous skin layer by an affinity driving force, wherein at least one of the organic compounds is a member of the group consisting of a herbicide, a pesticide, a polychlorinated biphenyl and a polycyclic aromatic hydrocarbon.

7. The method according to claim 6 wherein the nonporous skin layer comprises a polysiloxane deposited onto the microporous substrate from a gas plasma containing a disiloxane monomer.

8. The method according to claim 6 wherein the nonporous skin layer is overcoated with a coating comprising a polyfluorinated polymerizate deposited from a glow discharge plasma.

9. The method according to claim 8 wherein the perstraction membrane is in the form of a hollow fiber.

10. The method according to claim 9 wherein the concentration of the organic compound in the carrier fluid is measured by passing the carrier fluid through a sampling device of an analytical instrument.

11. The method according to claim 6 wherein the perstraction membrane is in the form of a hollow fiber.

12. The method according to claim 11 wherein the concentration of the organic compound in the carrier fluid is measured by passing the carrier fluid through a sampling device of an analytical instrument.

13. A method of determining organic contaminants in water comprising: a) bringing in a continuing manner an aqueous solution containing a plurality of organic compounds having Henry's constants of less than 0.0005 into contact with a first surface of a nonporous skin layer of a perstraction membrane, the nonporous skin layer having a first and a second surface, the perstraction membrane comprising a nonporous skin layer supported on its second surface by a microporous substrate, b) circulating a carrier fluid in contact with the second surface of the nonporous skin layer, and c) transferring in a continuing manner by perstraction a portion of the organic compounds from the aqueous solution through the nonporous skin layer to the carrier fluid until more than one of the organic compounds attain concentration levels in the carrier fluid that are at least 20-fold their concentration levels in the water, wherein the organic compounds are being transferred through the nonporous skin layer by an affinity driving force, and d) circulating the carrier fluid containing the organic compounds through a sampling device of an analytical instrument, wherein at least one of the organic compounds is a member of the group consisting of a herbicide, a pesticide, a polychlorinated biphenyl and a polycyclic aromatic hydrocarbon.

14. The method according to claim 13 wherein the analytical instrument is capable of identifying at least more than one of the organic compounds in the carrier fluid.

15. The method according to claim 14 wherein the organic compound is concentrated to a concentration level in the carrier fluid that is 20 to 10,000 fold greater than its concentration in the aqueous solution.

16. The method according to claim 14 wherein the membrane is contained in a membrane device having a first compartment for flow through of the aqueous solution and a second compartment for flow through of the carrier fluid.

17. The method according to claim 16 wherein the membrane is in the form of a hollow fiber.

18. The method according to claim 17 wherein the nonporous skin layer comprises a polysiloxane polymerizate deposited from a gas plasma containing a disiloxane monomer.

* * * * *

UNITED STATES PATENT AND TRADEMARK OFFICE
CERTIFICATE OF CORRECTION

PATENT NO. : 5,639,375
DATED : June 17, 1997
INVENTOR(S) : Hiroshi Nomura

It is certified that error appears in the above-indentified patent and that said Letters Patent is hereby corrected as shown below:

On the Title page, item [75] Inventor should be changed to read
--Hiroshi Nomura--.

Item [19] "Hiroshi" should read --Nomura--.

Signed and Sealed this

Twenty-eighth Day of October, 1997

Attest:

BRUCE LEHMAN

*Attesting Officer*       *Commissioner of Patents and Trademarks*